United States Patent
Isch et al.

(10) Patent No.: US 10,813,668 B2
(45) Date of Patent: Oct. 27, 2020

(54) POSTPARTUM HEMORRHAGE BALLOON SYSTEM

(71) Applicant: Cook Medical Technologies LLC, Bloomington, IN (US)

(72) Inventors: Andrew P. Isch, West Lafayette, IN (US); Victor Havill, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 157 days.

(21) Appl. No.: 16/117,997

(22) Filed: Aug. 30, 2018

(65) Prior Publication Data

US 2019/0069929 A1 Mar. 7, 2019

Related U.S. Application Data

(60) Provisional application No. 62/553,234, filed on Sep. 1, 2017.

(51) Int. Cl.
*A61B 17/42* (2006.01)
*A61B 17/12* (2006.01)
(Continued)

(52) U.S. Cl.
CPC ........ *A61B 17/42* (2013.01); *A61B 17/12036* (2013.01); *A61B 17/12136* (2013.01);
(Continued)

(58) Field of Classification Search
CPC .......... A61B 17/12036; A61B 17/1204; A61B 17/42; A61B 17/4241; A61B 17/442;
(Continued)

(56) References Cited

U.S. PATENT DOCUMENTS

| | | | | |
|---|---|---|---|---|
| 160,037 A | * | 2/1875 | Stillman | A61B 17/442 606/123 |
| 602,777 A | * | 4/1898 | Scroggs | A61F 6/16 128/836 |

(Continued)

FOREIGN PATENT DOCUMENTS

| WO | 106 237 483 | 12/2016 |
|---|---|---|
| WO | 106 264 644 | 1/2017 |

(Continued)

OTHER PUBLICATIONS

International Search Report and Written Opinion for PCT/US2018/048289, dated Jan. 7, 2019, 17 pp.

*Primary Examiner* — Ryan J. Severson
(74) *Attorney, Agent, or Firm* — Brinks Gilson & Lione

(57) ABSTRACT

A postpartum balloon system includes a flexible elongate catheter, an inflatable balloon, and a suction member attached to the distal end of the catheter. The system can be delivered into the uterus, where suction is applied to the suction member to anchor the balloon to the internal wall of the uterus. The catheter may include drainage ports both proximal and distal from the balloon. The system may include a stiffening stylet inserted into the drainage lumen of the catheter for aiding in delivery of the balloon. The stiffening stylet can be removed after placement of the balloon. The stiffening stylet can include side passageways that match the drainage ports and a lumen that allows for drainage through the stylet, as well as for administering drugs or other compounds through the drainage ports while the balloon is in place.

19 Claims, 3 Drawing Sheets

(51) Int. Cl.
*A61M 25/00* (2006.01)
*A61M 27/00* (2006.01)
*A61M 25/04* (2006.01)
*A61M 25/10* (2013.01)
*A61B 17/30* (2006.01)
*A61B 17/00* (2006.01)

(52) U.S. Cl.
CPC ............ *A61B 17/30* (2013.01); *A61M 25/007* (2013.01); *A61M 25/0082* (2013.01); *A61M 25/04* (2013.01); *A61M 25/10* (2013.01); *A61M 27/00* (2013.01); *A61B 17/1204* (2013.01); *A61B 17/12109* (2013.01); *A61B 2017/00557* (2013.01); *A61B 2017/12004* (2013.01); *A61B 2017/308* (2013.01); *A61B 2017/4216* (2013.01); *A61B 2217/005* (2013.01); *A61M 2025/1052* (2013.01); *A61M 2025/1061* (2013.01); *A61M 2210/1433* (2013.01)

(58) Field of Classification Search
CPC ...... A61B 2017/306; A61B 2017/4216; A61B 2217/005; A61F 6/14; A61F 6/146; A61F 6/16; A61F 6/18; A61M 2210/1433; A61M 25/04; A61M 29/00; A61M 25/007
See application file for complete search history.

(56) References Cited

U.S. PATENT DOCUMENTS

| | | | |
|---|---|---|---|
| 3,096,764 A | 7/1963 | Uddenbert | |
| 3,517,665 A | 6/1970 | Sheldon | |
| 4,571,239 A * | 2/1986 | Heyman | A61M 25/10 604/544 |
| 4,631,051 A * | 12/1986 | Harris | A61B 17/3415 604/164.01 |
| 4,863,424 A * | 9/1989 | Blake, III | A61M 25/0068 604/524 |
| 5,021,045 A * | 6/1991 | Buckberg | A61M 25/1002 604/101.04 |
| 6,676,680 B1 * | 1/2004 | Packer | A61B 17/12099 606/193 |
| 6,939,336 B2 * | 9/2005 | Silfver | A61M 31/00 128/898 |
| 7,220,252 B2 * | 5/2007 | Shah | A61M 25/1011 604/101.02 |
| 7,708,716 B2 * | 5/2010 | Shah | A61M 25/1011 604/101.02 |
| 8,123,773 B1 * | 2/2012 | Shirley | A61M 25/1002 604/103.07 |
| 9,125,686 B2 * | 9/2015 | Norred | A61B 17/42 |
| 9,364,638 B2 * | 6/2016 | Duncan | A61B 17/42 |
| 9,918,872 B1 * | 3/2018 | Crowson | A61F 7/0085 |
| 10,064,651 B2 * | 9/2018 | Norred | A61B 17/42 |
| 10,238,423 B2 * | 3/2019 | Odon | A61B 17/442 |
| 10,315,023 B2 * | 6/2019 | Mantri | A61B 17/12186 |
| 10,463,530 B2 * | 11/2019 | Booher, Sr. | A61F 6/08 |
| 2003/0236546 A1 | 12/2003 | Packer | |
| 2004/0230188 A1 * | 11/2004 | Cioanta | A61B 18/04 606/34 |
| 2005/0015047 A1 * | 1/2005 | Shah | A61M 25/1027 604/101.02 |
| 2005/0055043 A1 * | 3/2005 | Foltz | A61M 31/00 606/193 |
| 2006/0058831 A1 * | 3/2006 | Atad | A61M 25/1011 606/193 |
| 2006/0173486 A1 * | 8/2006 | Burke | A61B 17/12099 606/193 |
| 2006/0235461 A1 * | 10/2006 | Harter | A61M 25/0108 606/193 |
| 2007/0010708 A1 * | 1/2007 | Ness | A61B 17/3421 600/115 |
| 2007/0017527 A1 * | 1/2007 | Totz | A61M 16/0488 128/207.15 |
| 2007/0239110 A1 * | 10/2007 | Shah | A61M 25/1011 604/96.01 |
| 2008/0081829 A1 * | 4/2008 | Isch | A61L 31/06 514/354 |
| 2008/0243103 A1 * | 10/2008 | Whetham | A61M 25/10 604/515 |
| 2009/0192542 A1 * | 7/2009 | Harter | A61B 17/42 606/193 |
| 2013/0041352 A1 * | 2/2013 | Smith | A61M 25/0017 604/544 |
| 2013/0245637 A1 * | 9/2013 | Norred | A61B 17/42 606/119 |
| 2014/0074110 A1 * | 3/2014 | Norred | A61B 17/42 606/119 |
| 2014/0188126 A1 * | 7/2014 | Odon | A61B 17/42 606/122 |
| 2015/0202411 A1 * | 7/2015 | Duncan | A61B 17/42 604/544 |
| 2015/0265456 A1 * | 9/2015 | Booher, Sr. | A61F 6/08 128/836 |
| 2017/0290605 A1 * | 10/2017 | Bakri | A61M 25/0026 |
| 2018/0055523 A1 * | 3/2018 | Bair | A61B 17/22004 |
| 2018/0221196 A1 * | 8/2018 | Crowson | A61F 7/106 |
| 2018/0264247 A1 * | 9/2018 | Mantri | A61B 90/39 |
| 2018/0360494 A1 * | 12/2018 | Melsheimer | A61B 17/12099 |
| 2019/0053828 A1 * | 2/2019 | Prior | A61B 17/4241 |
| 2019/0059947 A1 * | 2/2019 | Bunch | A61B 17/12136 |
| 2019/0069929 A1 * | 3/2019 | Isch | A61B 17/12136 |
| 2019/0083132 A1 * | 3/2019 | Norred | A61B 17/42 |
| 2019/0110797 A1 * | 4/2019 | Melsheimer | A61B 17/12136 |
| 2019/0216504 A1 * | 7/2019 | Norred | A61B 17/42 |
| 2019/0231359 A1 * | 8/2019 | Mantri | A61B 17/1204 |
| 2019/0232036 A1 * | 8/2019 | Mantri | A61B 17/12045 |
| 2019/0232037 A1 * | 8/2019 | Mantri | A61N 5/1015 |
| 2019/0232038 A1 * | 8/2019 | Mantri | A61N 5/00 |
| 2020/0093498 A1 * | 3/2020 | Roberts | A61B 17/12099 |

FOREIGN PATENT DOCUMENTS

| | | |
|---|---|---|
| WO | 106 821 472 | 6/2017 |
| WO | WO 2018/029250 A1 | 1/2018 |

* cited by examiner

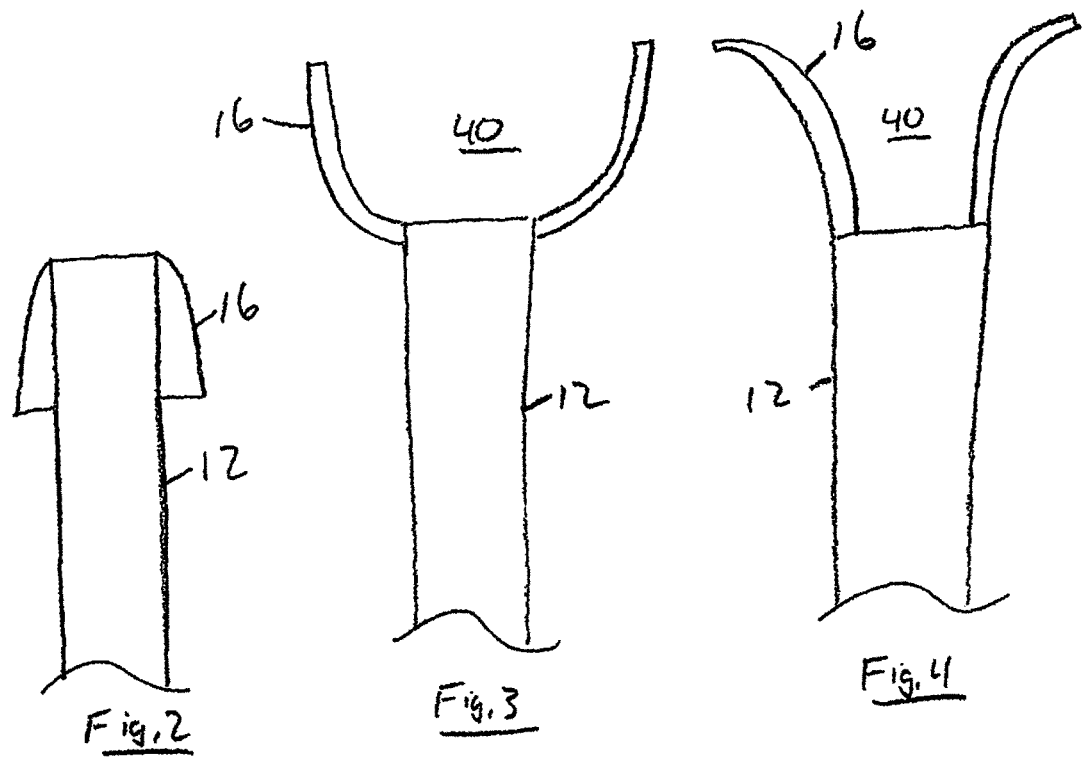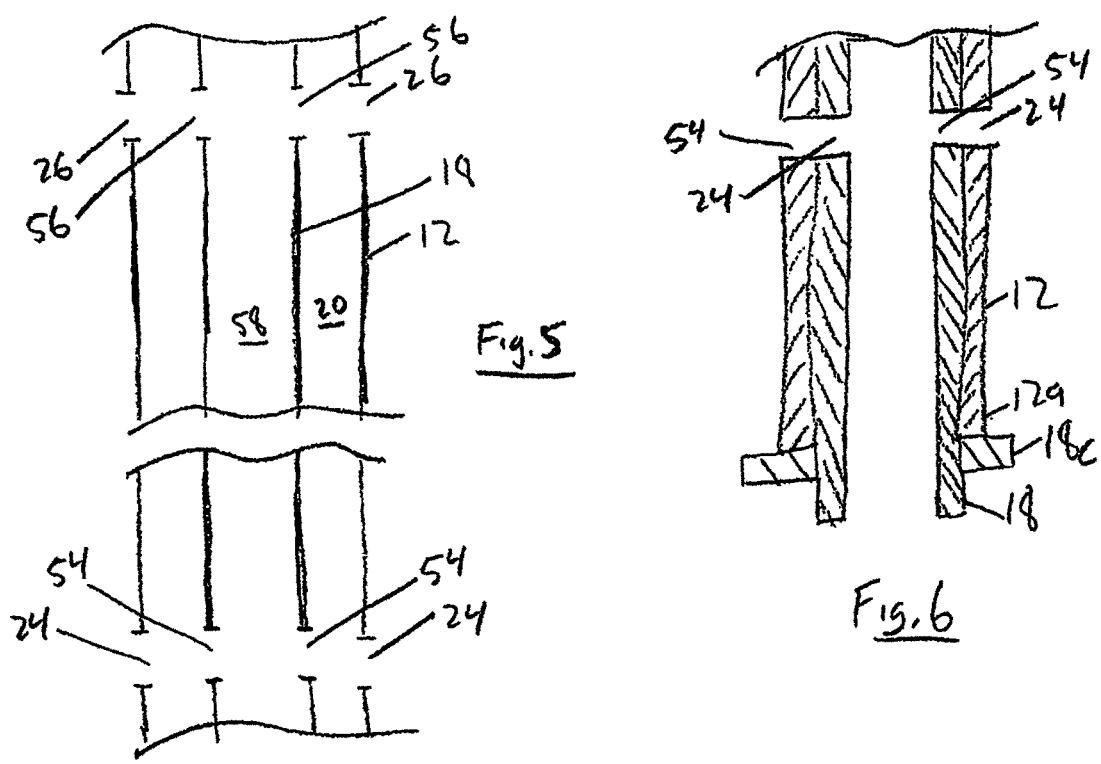

POSTPARTUM HEMORRHAGE BALLOON SYSTEM

CROSS-REFERENCE TO RELATED APPLICATIONS

This application claims priority from U.S. Provisional Application No. 62/553,234, filed on Sep. 1, 2017, the entirety of which is hereby fully incorporated by reference herein.

BACKGROUND

1. Technical Field

The present disclosure relates to medical devices. More particularly, the disclosure relates to a postpartum hemorrhage balloon system.

2. Background Information

Blood loss during childbirth is a common occurrence in women. Women undergoing C-sections will typically lose more blood than women that deliver vaginally. A normal occurrence during childbirth includes the separation of the placenta from the uterus, which results in open blood vessels in the uterus. In many instances, natural contraction of the uterus after childbirth will cause the blood vessels to close.

In some cases, women may continue to experience bleeding in the uterus that is not resolved by typical uterine contraction. Instances of excessive bleeding can be referred to as a postpartum hemorrhage, or "PPH." PPH must be treated quickly to limit the amount of blood loss to the woman.

One method of treating PPH involves the physician massaging or manually compressing the uterus with her hands to stop the excessive bleeding. However, this approach is only a short term solution and may not be effective for many instances of PPH.

Another approach for treating PPH includes the use of an inflatable balloon inserted into the uterus through the cervix and inflated to provide an outward force on the internal wall of the uterus. However, placement and retention of the balloon can be subject to the patient's anatomy. In some cases, the balloon may not be adequately retained even when fully inflated when the cervix is fully dilated, and the balloon may slide out of the patient.

Further, the balloon is typically delivered using a flexible silicone catheter, which remains in place and provides for drainage from the uterus. Because the catheter remains in place for drainage, the flexible nature provides for more comfortable experience for the patient. However, this can make placement of the balloon difficult due to the flexible nature of the catheter.

Also, once the balloon has been placed and inflated within the uterus, it becomes difficult to deliver treatments to the patient, such as hemostatic or uterotonic compounds or API.

Accordingly, improvements can be made in the use of inflatable balloons for treating PPH.

SUMMARY

The present disclosure provides a system for treating postpartum hemorrhage. The system includes an elongated catheter having a proximal end and a distal end, a suction member attached to the distal end of the catheter, and an inflatable balloon attached to the catheter proximally relative to the suction member.

The system further includes a first lumen extending through the catheter in fluid communication with a cavity defined by the suction member, the first lumen configured to apply a vacuum force to the suction member. A second lumen extends through the catheter that is in fluid communication with the inflatable balloon and configured to deliver inflation fluid to the balloon to inflate the balloon.

The system may further include at least one distal drainage port of the catheter located between the balloon and the suction member, at least one proximal drainage port of the catheter located proximal from the balloon, and a third lumen in fluid communication with the distal drainage port and the proximal drainage port.

In one approach, the system may include a stiffening stylet disposed within a third lumen of the catheter, the stiffening stylet being stiffer than the catheter for providing support to the catheter.

In one form, the stylet includes a stylet lumen and at least one proximal passageway and at least one distal passageway, wherein the proximal and distal passageways provide fluid communication from the stylet lumen to an exterior of the stylet.

The proximal and distal passageways of the stylet may be spaced apart longitudinally at a length that corresponds to a longitudinal spacing of the proximal and distal drainage ports of the catheter.

The system may include a proximal hub, such as luer hub, that may be attached to a suction device that is in in communication with the first lumen of the catheter. The suction device may include a retractable plunger for applying a suction force to the first lumen and suction member. The retractable plunger maybe a locking plunger to apply and hold the applied suction force.

In one form, the suction member is in the form of a suction cup having a distally facing concave shape. In one approach, the suction cup is flexible and resilient and biased to the distally facing concave shape, the suction cup being capable of temporarily folding over to have a concave shape facing proximally in response to insertion through a constriction, wherein the suction cup will return to the distally facing concave shape after passing through the constriction.

The present disclosure further provides a method of treating postpartum hemorrhage. The method includes providing a medical device system including an elongate catheter having a proximal and a distal end and an inflatable balloon attached to a distal portion of the catheter, and a suction member attached to the distal end of the catheter and disposed distally from the balloon. The method further includes delivering the catheter and suction member into a body cavity, and delivering the suction member into contact with an internal wall of the body cavity.

The method further includes applying a suction force to the suction member via a suction lumen extending through the catheter, and in response to applying the suction force, anchoring the catheter to the internal wall of the body cavity. The method further includes, in response to anchoring the catheter, inflating the balloon via an inflation port of the catheter.

In one approach, the catheter includes at least one proximal drainage port disposed proximally relative to the balloon and at least one distal drainage port disposed between the suction member and the balloon, and the catheter further includes a drainage lumen in fluid communication with the drainage ports. The method may further include receiving fluid into the drainage lumen through each of the drainage ports.

In one approach, the system further includes a stylet extending into the drainage lumen of the catheter, wherein the catheter and stylet are delivered together.

In one form, the stylet includes a stylet lumen and proximal and distal passageways in fluid communication with the stylet lumen, where the passageways aligned with the proximal and distal drainage ports when the stylet is inserted within the drainage lumen of the catheter. The method may further include delivering a compound through the stylet lumen, through the passageways, and through the drainage ports into the body cavity.

In one approach, after inflating the balloon, the method includes removing the stylet from the drainage lumen, and after removing the stylet, inserting the stylet into the drainage lumen and delivering a compound through a lumen of the stylet, through at least one passageway defined by the stylet, and through at least one of the proximal and distal drainage ports into the body cavity.

In one approach, fluid from the body cavity drains through a lumen of the stylet via at least one passageway defined through a wall of the stylet.

BRIEF DESCRIPTION OF THE DRAWINGS

FIG. 2 illustrates the suction member in a folded over state;

FIG. 3 illustrates another embodiment of the suction member;

FIG. 4 illustrates a further embodiment of the suction member;

FIG. 5 illustrates drainage ports of the catheter and passageways of the stylet being aligned with each other when the stylet is inserted within the catheter;

FIG. 6 illustrates the stylet inserted into the catheter with a stop member of the stylet controlling the depth of the insertion;

DETAILED DESCRIPTION

The present invention provides a postpartum hemorrhage balloon that can be anchored within the uterus and including a delivery stylet. The disclosure provides also for methods of treatment. The materials, methods, and examples disclosed herein are illustrative only and not intended to be limiting. The disclosed figures are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which this disclosure pertains. In the case of conflict, the present document and definitions will control.

The terms "proximal" and "distal" and derivatives thereof will be understood in the frame of reference of a medical physician using the device. Thus, proximal refers to locations closer to the physician and distal refers to locations farther away from the physician (e.g., deeper in the patient's vasculature).

Figure 1:
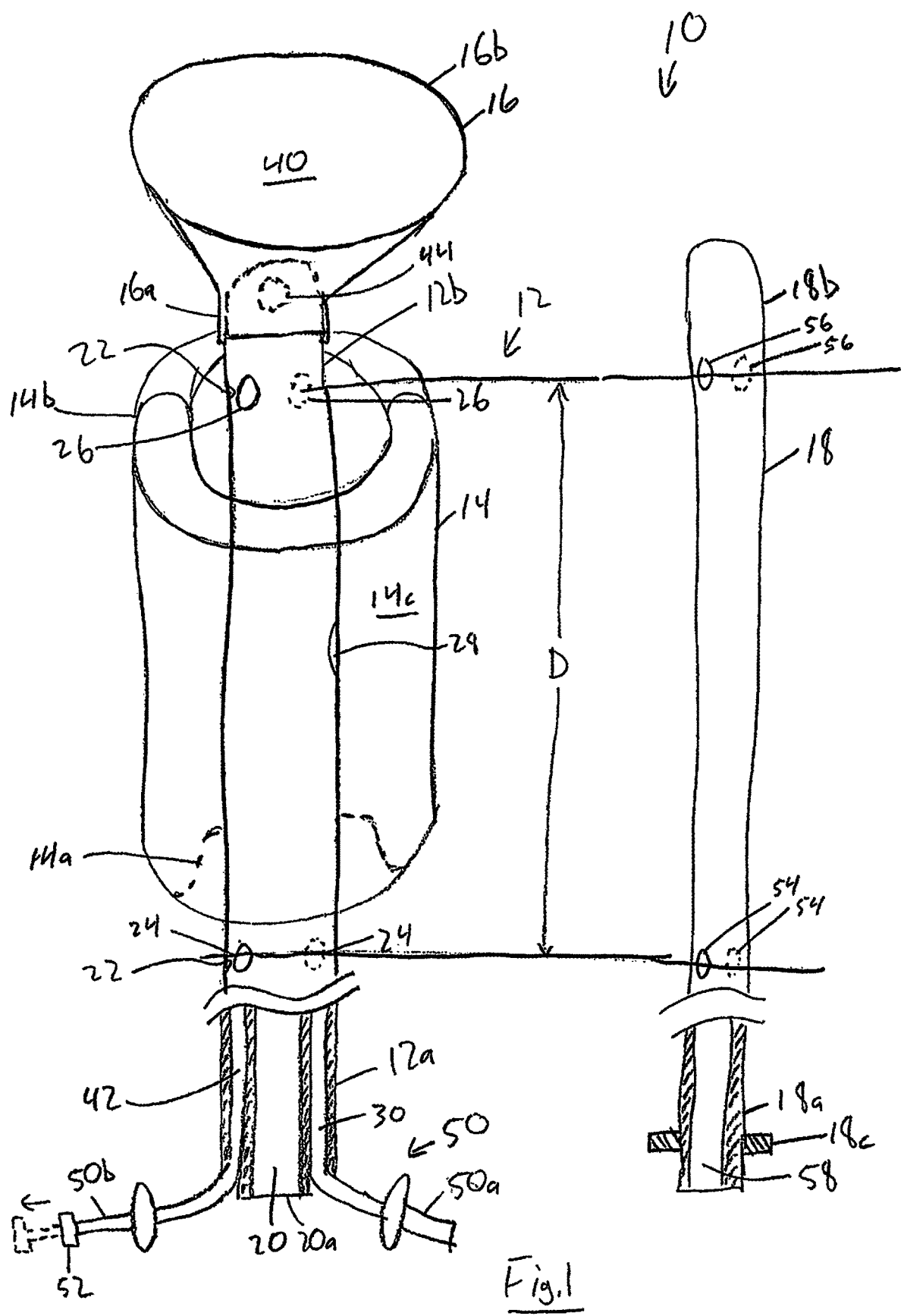
FIG. 1 illustrates a system for treating postpartum hemorrhage including a flexible catheter, an inflatable balloon coupled to the catheter, a suction member attached to a distal end of the catheter, and stiffening stylet receivable within the catheter.

FIG. 1 illustrates a system 10 for treating postpartum hemorrhage. The system 10 includes an elongate or elongated flexible catheter 12 having an inflatable balloon 14 coupled to the catheter 12 at a distal portion of the catheter 12. The system 10 further includes a suction member 16 attached to the distal end of the catheter 12. The system 10 may further include an elongate stylet 18 that is sized and configured to be inserted into the flexible catheter 12 to provide stiffness to the catheter 12 when the stylet 18 is inserted therein.

With regard to the catheter 12, the catheter 12 may be in the form of a traditional flexible silicone catheter commonly used in treating postpartum hemorrhage for delivering an inflatable balloon to the uterus through the cervix. The catheter 12 has an elongate form and includes a proximal end 12a and a distal end 12b. The catheter 12 may include multiple lumens extending from the proximal end 12a toward the distal end 12b. The lumens, further described below, may be coaxial or axially offset.

The catheter 12 may include a drainage lumen 20 extending from the proximal end 12a toward the distal end 12b, with the drainage lumen 20 defining a proximal opening 20a located at the proximal end 12a of the catheter 12. The drainage lumen 20 extends from the proximal opening 20a in a distal direction toward one or more drainage ports 22, with the drainage lumen 20 being in fluid communication with the drainage ports 22 such that fluid outside of the catheter 12 can flow through the ports 22 into drainage lumen 20 and can flow through the drainage lumen 20 toward and out of the proximal opening 20a of the drainage lumen 20. It will be appreciated that the drainage lumen 20, being in fluid communication with the exterior of the catheter 12 to receive fluid into drainage lumen, is thereby arranged within the catheter 12 to access the exterior of the catheter 12.

The drainage ports 22 can include proximal drainage ports 24 and distal drainage ports 26. The distal drainage ports 26 are disposed distally from the balloon 14. The proximal drainage ports 24 are disposed proximally from the balloon 14. Both the distal drainage ports 26 and the proximal drainage ports 24 are in fluid communication with the drainage lumen 20.

The number of proximal drainage ports 24 and distal drainage ports 26 can vary depending in the needs of the patient. In one approach, there are two proximal drainage ports 24 located on opposite sides of the catheter 12 from each other, and two distal drainage ports 26 located on opposite sides of the catheter 12 from each other. However, it will be appreciated that the drainage ports 24 and/or 26 can be arranged such that they are not on opposite sides of the catheter 12, but rather on the same side lateral side of the catheter 12. Further, there could be three or more proximal drainage ports 24 and/or three or more distal drainage ports 26, or a single drainage port 24 and a single drainage port 26. The spacing of the drainage ports 24, 26 around the circumference of the catheter 12 can be the same between each of the ports, or the spacing can vary, such that some of the drainage ports 24 or 26 may be circumferentially closer to each other than others.

The proximal drainage ports 24 are preferably located at the same longitudinal position as each other. However, it will be appreciated that one or more of the multiple proximal drainage ports 24 could be located at a different longitudinal position relative to the other proximal drainage ports 24.

The distal drainage ports 26 are preferably located at the same longitudinal position as each other. However, it will be appreciated that one or more of the multiple distal drainage ports 26 could be located at a different longitudinal position relative to the other distal drainage ports 26.

The drainage ports 24, 26 can have a generally circular shape, or they could have other shapes, such as polygonal shapes, oval shapes, slots, or other known drainage port shapes. The shapes of the drainage ports 24, 26 could be the same, or could be different relative to each other.

For the purposes of further discussion, the proximal drainage ports 24 will be described as being at the same longitudinal position, with two ports on diametrically opposite sides of the catheter 12, and the distal drainage ports 26 will be described as being at the same longitudinal position, with two ports on diametrically opposite sides of the catheter 12. In this approach, there is a longitudinal distance D between the respective longitudinal positions of the proximal and distal drainage ports 24, 26. It will be appreciated that other arrangements of drainage ports would result in various different longitudinal distances between selected ones of the proximal drainage ports 24 and selected ones of the distal drainage ports 26.

In an embodiment where the stylet 18 is included, as further described below, the spacing of the drainage ports 24 and/or 26 is preferably selected to correspond to the spacing of corresponding ports of the stylet.

With regard to the balloon 14, the balloon 14 is preferably in the form of a traditional inflatable balloon for use in internal uterine compression for treating PPH, such as the Cook Bakri Balloon. The balloon 14 is inflatable from a radially compressed delivery configuration to a radially expanded and inflated configuration, in which the balloon 14 will exert on outward force on the internal surface of the uterus. The balloon 14 is preferably delivered to the uterus in the compressed delivery configuration through the cervix, and then radially expanded and deployed into the inflated configuration once delivered within the uterus.

The balloon 14 is attached to the catheter 12 in manner known in the art, with a proximal end 14a of the balloon attached to the catheter 12, and the distal end 14b of the balloon also attached to the catheter 12. The balloon 12 defines an internal cavity 14c that is fluidly isolated from the exterior of the balloon 14, such that introduction of fluid into the cavity 14c will cause the balloon 14 to expand.

The catheter 12 includes an inflation port 28 that is in fluid communication with the cavity 14c of the balloon 14. The catheter 12 includes an inflation lumen 30 that extends from the proximal end 12a of the catheter to the inflation port 28, such that there is fluid communication between the cavity 14c and the inflation lumen 30. Inflation fluid is thereby provided through the catheter 12 via the inflation lumen 30 into the cavity 12c for inflating the balloon 14. The balloon 14 may be inflated or deflated by controlling the amount of inflation fluid that is introduced or removed from within the cavity 14c via the inflation lumen 30.

The proximal drainage ports 24 are located on the catheter 12 proximally from the proximal end 14a of the balloon 14. The distal drainage ports 26 are located distally from the distal end 14b of the balloon 14. Thus, the attachment points of the balloon 14 to the catheter 12 are located between the proximal drainage ports 24 and the distal drainage ports 26.

After inflation of the balloon 14, portions of the inflated balloon 14 may extend proximally or distally beyond the respective drainage ports, but the balloon 14 will extend away from the catheter 12 in the location of the ports 24, 26 such that the ports 24, 26 are not blocked. Thus, with the balloon 14 in an inflated configuration, fluid within the uterus can still drain out of the uterus through the drainage ports 24, 26.

The balloon 14 is attached to the catheter proximally from the distal end 12b of the catheter 12, such that there is space on the catheter 12 to accommodate the distal drainage ports 26, as well as the suction member 16 that is attached to the catheter 12 distally from the distal drainage ports 26. The balloon 14 is attached to a distal portion of the catheter 12, such that it is adjacent the distal end 12b.

With regard to the suction member 16, the suction member 16 is attached to the distal end 12b of the catheter 12. The suction member 16 may be attached to the terminal end of the catheter 12, such that the distal end 12b of the catheter 12 terminates near the attachment between the suction member 16 and the catheter 12. In one form, the distal end 12b may extend slightly beyond the attachment between the suction member 16 and the catheter 12, or it may terminate at the attachment.

With reference to FIGS. 1-4, the suction member 16 is preferably in the form of a suction cup. In this form, the suction member 16 has a proximal end 16a attached to the distal end 12b of the catheter 12, and a distal end 16b defining the distal end of the assembly of the suction member 16 and catheter 12. The proximal end 16a is narrower than the distal end 16b, such that the suction member 16 has a tapered shape that tapers outward in a distal direction.

The suction member 16 therefore has a concave shape facing distally, and a convex shape facing proximally. The concave shape of the suction member 16 thereby defines a distally facing recess 40 within the suction member 16. This distally facing recess is configured to contact an interior surface of the uterus to apply suction thereto and anchor the distal end of the catheter 12 to the internal surface of the uterus.

To apply suction to the suction member 16, the catheter 12 includes a suction lumen 42 that extends from the proximal end 12a of the catheter 12 to the distal end 12b of the catheter 12. The catheter 12 further includes a distal suction port 44 at the distal end of the suction lumen 42, such that the suction port 44 is in fluid communication with the suction lumen 42. The suction port 44 is also in fluid communication with the recess 40 of the suction member 16, such that the recess 40 is in fluid communication with the suction lumen 42.

The suction member 16 is preferably made from a thin and flexible silicone material. This flexible material may allow the suction member 16 to fold over itself (FIG. 2) during delivery of the system 10 through the cervix. In this embodiment, the suction member 16 is resilient and biased toward the shape described above, such that if the suction member 16 folds over itself and becomes everted, the suction member 16 will pop back to having a distally facing concave shape. In this form, the suction member 16 can be delivered without having a dedicated compressed delivery configuration and expanded deployed configuration, as the cervix is typically dilated to a sufficient degree such that the suction member 16 can pass through, and flex if necessary.

The suction member 16 can have a conical shape with generally flat walls when viewed in cross-section (FIG. 1), or it may have a cup shape, with curved walls (FIG. 2). The concave recess 40 can be defined by convex walls that define a horn-shape (FIG. 3), where the overall recess is open distally and overall concave, but the walls in cross-section have a convex shape. It will be appreciated that various other shapes of the suction member 16 can be used which include the distally facing recess 40. The degree of taper of the suction member 16 can be constant or variable, and the magnitude of the taper can also vary depending on the needs of the patient, such that the recess 40 may be relatively shallow or relatively deep. The cross-section of the suction member 16 can also have a complex curvature that is both convex and concave at different locations.

As described above, the catheter 12 includes multiple lumens, including the drainage lumen 20, the inflation lumen 30, and the suction lumen 42. Each of these lumens extend from the proximal end 12a of the catheter 12, but they extend distally to different longitudinal locations through the catheter 12. For example, the suction lumen 42 extends fully through the catheter 12 to reach the recess 40 of the suction member. The inflation lumen 30 extends at least to the inflation port 28 of the balloon 14, but does not extend fully through catheter 12. Preferably, the inflation lumen 30 terminates at the inflation port 28. The drainage lumen 20 extends at least to the distal drainage ports 26, but does not extend fully through the catheter 12.

Thus, the drainage lumen 20 preferably extends a longer distance than the inflation lumen 30, but a shorter distance than the suction lumen 42. However, in embodiments that do not include distal drainage ports 26, the drainage lumen may extend only to the proximal drainage ports 24, and would therefore be shorter than the inflation lumen 30. In one approach, multiple drainage lumens could be used, where one lumen extends to the distal drainage ports 26, and another lumen extends to the proximal drainage ports 24.

With reference again to FIG. 1, the proximal end 12a of the catheter 12 may include a hub 50 in the form of a luer hub that allows the physician to operate and manage drainage, suction, and inflation. The hub 50 may include an inflation port 50a that can be selectively opened or closed and connected to a source of inflation fluid in a manner known in the art.

The hub 50 may further include a suction port 50b for attachment to a suction device or suction source, such as a syringe. In one approach, the suction port 50b is attached to a syringe 52 that can apply suction through the suction lumen 42 to the recess 40 in response to retracting the plunger syringe 52. The syringe 52 may be in the form of a retractable, locking plunger for applying and holding a suction force through the suction lumen 42 and to the suction member 16. The suction syringe 52 has been verified to provide sufficient suction to hold a traditional Bakri Balloon filled with 1 liter (1000 g) of water. The suction source may also be in the form an attached vacuum device or pump or other mechanism configured to produce suction through an attached lumen or passageway.

Thus, the suction member 16 provides an anchoring mechanism when the suction member 16 is pressed against the internal wall of the uterus, and the suction force is applied. With this suction force applied, a patient could stand up without the balloon 14 falling out, unlike in many non-anchored balloons. A further benefit of applying the suction is that standing or sitting upright with the suction applied, or applying traction to the balloon manually, could aid in uterine involution, which is not possible for balloons that are not anchored.

Referring to FIGS. 1, 5, and 6, with regard to the stylet 18, the stylet 18 is in the form an elongate or elongated rod having a stiffness that is preferably greater than the stiffness of the catheter 12. The stylet 18 is preferably formed of a biocompatible material. The stylet 18 has a proximal end 18a and a distal end 18b. When inserted into the catheter 12, the stylet 18 provides additional stiffness and pushability to the catheter 12 relative to a similarly flexible catheter without a stylet.

The stylet 18 is sized and configured to extend into the drainage lumen 20 of the catheter 12 to provide additional stiffness to the catheter 12 to improve delivery and placement of the balloon 14, as shown in FIGS. 5 and 6. Thus, the stylet 18 preferably has a diameter that generally corresponds to the inner diameter of the drainage lumen 20, as shown in FIG. 6.

The stylet 18 may further include passageways extending through the side of the stylet 18, which allows for drainage to flow into the interior of the stylet or for drugs to be delivered to the uterus via the interior of the stylet. More particularly, the stylet 18 may include proximal passageways 54 and distal passageways 56 that are disposed at locations on the stylet 18 that match the locations of the proximal and distal drainage ports 24 and 26, respectively. The stylet further includes a stylet lumen 58 that extends from the proximal end 16a at least to the distal passageways 56, thereby providing fluid communication between the stylet lumen 58 and the distal passageways 56 as well as proximal passageways 54.

Thus, as shown in FIG. 5, when the stylet 18 is inserted into the drainage lumen 20, the proximal and distal ports 24 and 26 will not be blocked from draining. Rather, drainage occurring through the drainage ports 24 and 26 will pass through the passageways 54 and 56 and into the stylet lumen 58. FIG. 5 is a schematic illustration and shows stylet 18 within the drainage lumen 20, and the drainage lumen 20 appears large enough for drainage to occur through both lumens 20 and 58. The amount of drainage through the lumen 20 when the stylet 18 is inserted within the catheter 12 will depend on the different sizes of the stylet 18 and the catheter 12. In one approach, the sizes are comparable, such that the drainage lumen 20 is substantially filled with the stylet 18, such that there is nominal space between the stylet and the catheter 12.

The stylet 18 therefore preferably includes a number and arrangement of passageways 54, 56 that correspond to the number and arrangement of drainage ports 24, 26. However, there could be additional stylet passageways that do not match up with the drainage ports 24, 26 while still allowing for drainage through the other matched ports and passageways.

As described above, the drainage ports 24, 26 could have different spacing relative to each other, and the stylet passageways 54, 56 can likewise have different spacing relative to each other. For purposes of discussion, the stylet 18 will be described as having two proximal passageways 54 on diametrically opposite sides and the same longitudinal location, and two distal passageways 56 on diametrically opposite sides and the same longitudinal location.

As shown in FIG. 1, the longitudinal distance between the proximal and distal passageways 54, 56 of the stylet preferably corresponds to the distance D between the proximal and distal drainage ports 24, 26 such that each of the ports and passageways of the catheter 12 and the stylet 18 can be aligned. It will be appreciated that different spacing of the ports 24, 26 can also be matched by corresponding different spacing of the passageways 54, 56.

The stiffening stylet 18 may include a stop member 18c disposed near the proximal end 18a that operates to abut the proximal end 12a of the catheter 12 to aid in aligning the ports 24, 26 and passageways 54, 56, as shown in FIG. 6.

The stiffening stylet 18 can therefore provide for improved delivery of the system 10 without clogging the drainage ports 24, 26. Further, the stylet 18 may allow for delivery of drugs or other fluidic compounds to the patient. For example, a hemostatic material, such as Cook Hemospray, or uterotonic drugs can be delivered to the inside of the uterus through the stylet 18, where the drugs or compounds will exit through the passageways 54, 56 and drainage ports 24, 26 and into the interior of the uterus. After delivering the drugs or compound through the stylet 18, the stylet 18 may be removed. The stylet can later be inserted back into the catheter 12 if additional drugs or compounds are desired.

Having described the general structure of the system 10, a method of using the system 10 will now described.

Figure 8:
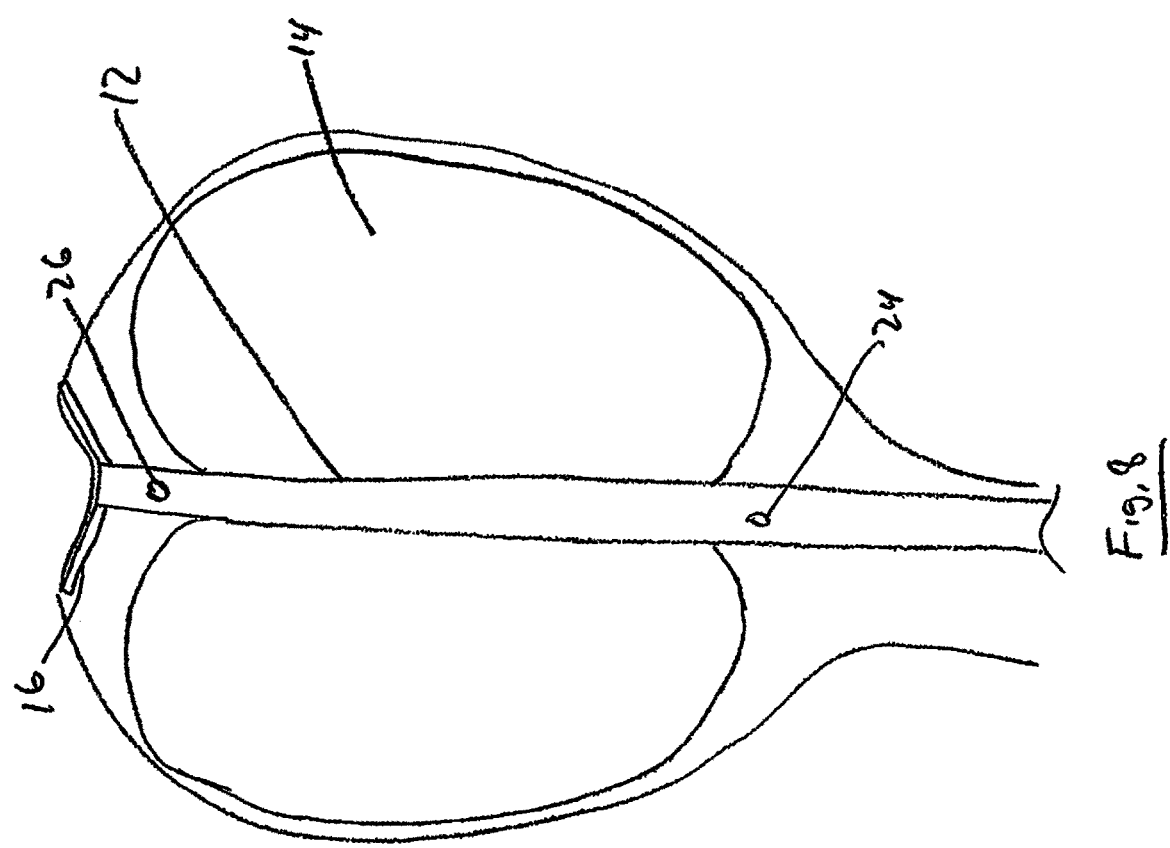
FIG. 8 illustrates the system in an anchored position within the uterus.
Figure 7:
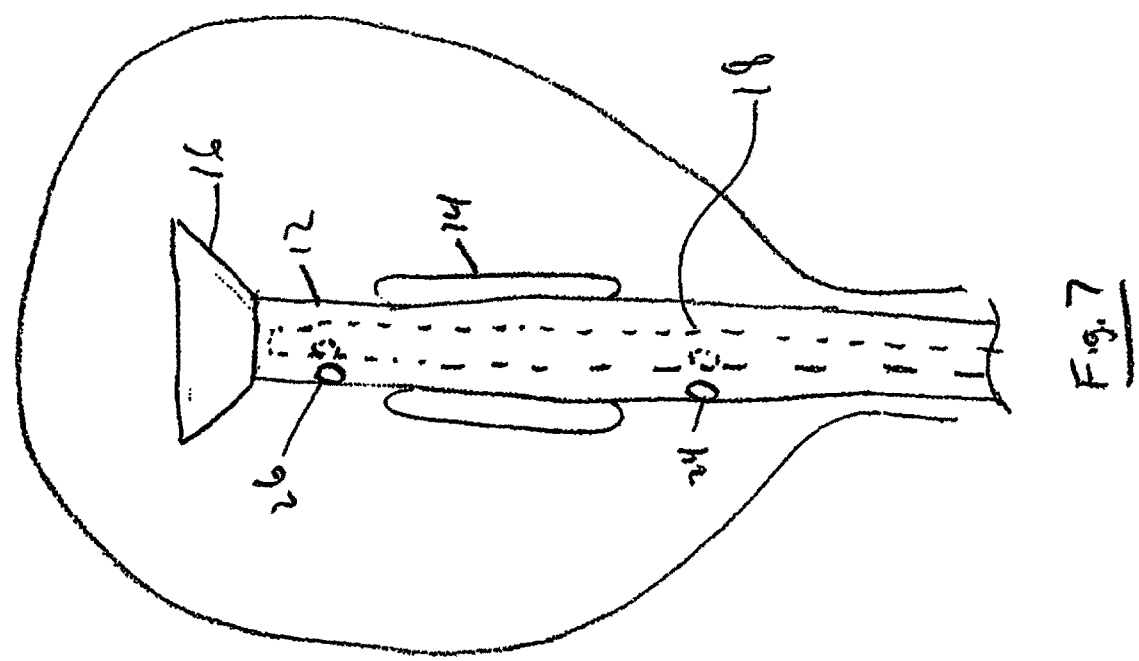
FIG. 7 illustrates the system inserted into the uterus prior to anchoring the catheter.

With reference to FIGS. 7 and 8, to treat the postpartum hemorrhage condition in the patient, the physician may provide the system 10 with the catheter 12 and the suction 16 member on the distal end thereof, along with the stylet 18 inserted into the drainage lumen 20 of the catheter 12. The configuration may be referred to as the delivery configuration.

In the delivery configuration, the system 10 has a stiffness that generally corresponds to the stiffness of the stylet 18. Thus, the stiffness of the system 10 is greater than the stiffness of the generally flexible catheter 12.

The stylet 18 and catheter 12 may be inserted into the uterus through the cervix. The stiffness provided by the stylet 18 gives the system 10 additional pushability and improved control to the physician relative to a system without a stiffening stylet.

As the distal end of the system 10 is inserted through the cervix into the uterus, the suction member 16 may flex and fold back over itself. Once the suction member 16 has passed through the cervix into the interior of uterus, the suction member 16 can pop back to its nominal shape due to the resilient nature of the suction member 16.

The catheter 12 may be advanced up into the uterus, such that the suction member 16 will come into contact the top of the uterus, as shown in FIG. 8. The physician may monitor the progression of the catheter 12 and suction member 16 through known methods to determine when the suction member 16 has made contact with the top of the uterus. In one form, the physician may perceive that the suction member 16 has made contact with the top of the uterus by the catheter 12 being limited from further insertion.

With the suction member 16 contacting the top of the uterus, the physician may provide suction to the suction member 16 by actuating the suction source. In the case of the plunger 52, the physician may retract the plunger 52, thereby creating a negative pressure through the suction lumen 42. The negative pressure or vacuum created through the suction lumen 42 will be transmitted through the suction lumen 42 and into the recess 40. Applying this negative pressure to the recess 40 will cause the suction member 16 and uterine tissue to be drawn together, creating a suction effect and anchoring the suction member 16 to the internal wall of the uterus. The suction will remain active while the plunger 52 is in its actuated and retracted position. The plunger 52 may be locked in place to maintain the suction force that is applied to the uterus.

With the suction member 16 anchored to the uterine wall, the catheter 12 and balloon 14 are likewise held in place. With the catheter 12 and balloon 14 in place, the balloon 14 may be inflated by introducing inflation fluid into the balloon 14 through the inflation lumen 30 in a manner known in the art. The balloon 14 will expand outward in response to receiving the inflation fluid, and the balloon 14 will thereby contact the uterine wall and provide a compressive force to the internal wall of the uterus to promote hemostasis and treat the postpartum hemorrhage, as illustrated in FIG. 8.

Before or after the balloon 14 is inflated, fluid such as blood may be present in the uterus, where drainage is desirable. With the catheter 12 inside the uterus, this blood or other fluid can drain out of the uterus through the drainage ports 24 and 26. Distal drainage ports 26 provide a path for blood present at the top of the uterus to drain. It has been observed that hemorrhaging is more present at the top of the uterus than at the bottom, so the distal drainage ports 26 provide a path for the drainage of the this blood, even after the balloon 14 has been inflated, which could otherwise block the blood from flowing down out of the uterus. The proximal drainage ports 24 provide a path for drainage of blood that is present at the bottom of the uterus.

As described above, the stylet 18 includes passageways 54, 56 that align with the ports 24, 26 of the catheter 12, such that drainage can occur during delivery of the system 10 when the stylet 18 is present and before removal of the stylet 18. Thus, the stylet 18 can remain in place to ensure effective placement of the system 10 without compromising the drainage out of the uterus. With the stylet 18 in place, drainage may pass through the stylet lumen 58 in addition to the drainage lumen 20 or alternative to the drainage lumen 20, depending on the relative diameters of the stylet 18 and the drainage lumen 20.

With the catheter 12, balloon 14, and suction member 16 anchored within the uterus, the stylet 18 may be removed, thereby leaving behind the more flexible and comfortable catheter 12. The stylet 18 can be reintroduced to the catheter 12 at a later time to deliver drugs or other compounds through the stylet 18 and out of the ports of the catheter 12 into the uterus as desired by the physician to treat the patient. Similarly, in the event that the balloon needs to be repositioned or suction re-applied, the stylet 18 can easily be reinserted into the catheter 12 to provide support for additional positioning.

When treatment is completed, the plunger 52 may be actuated and advanced to provide a positive pressure to the suction member 16 that will release the suction member 16 from the uterine wall. The balloon 14 may be deflated using known methods, and the catheter 12, balloon 14, and suction member 16 may be removed back through the cervix.

The above described system and method may be used to provide internal compression to the uterus in addition to other systems and methods that provide external compression to the uterus.

While the present invention has been described in terms of certain preferred embodiments, it will be understood that the invention is not limited to these disclosed embodiments as those having skill in the art may make various modifications without departing from the scope of the following claims.

The invention claimed is:

1. A system for treating postpartum hemorrhage, the system comprising:
   an elongated catheter having a proximal end and a distal end;
   a suction member attached to the distal end of the catheter;
   an inflatable balloon attached to the catheter proximally relative to the suction member;
   a first lumen extending through the catheter in fluid communication with a cavity defined by the suction member, the first lumen configured to apply a vacuum force to the suction member;

a second lumen extending through the catheter in fluid communication with the inflatable balloon and configured to deliver inflation fluid to the balloon to inflate the balloon; and at least one distal drainage port of the catheter located between the balloon and the suction member, at least one proximal drainage port of the catheter located proximal from the balloon, and a third lumen in fluid communication with the distal drainage port and the proximal drainage port.

2. The system of claim 1, further comprising a stiffening stylet disposed within a third lumen of the catheter, the stiffening stylet being stiffer than the catheter for providing support to the catheter.

3. The system of claim 1, further comprising a stylet disposed within the third lumen of the catheter.

4. The system of claim 3, wherein the stylet includes a stylet lumen and at least one proximal passageway and at least one distal passageway, wherein the proximal and distal passageways provide fluid communication from the stylet lumen to an exterior of the stylet.

5. The system of claim 4, wherein the proximal and distal passageways of the stylet are spaced apart longitudinally at a length that corresponds to a longitudinal spacing of the proximal and distal drainage ports of the catheter.

6. The system of claim 3, wherein the stylet is stiffer than the catheter.

7. The system of claim 1, further comprising a proximal hub having an attached suction device in communication with the first lumen of the catheter.

8. The system of claim 7, wherein the suction device includes a retractable plunger for applying a suction force to the first lumen and the suction member.

9. The system of claim 7, wherein the proximal hub further includes an inflation port in communication with the second lumen of the catheter for providing inflation fluid to the balloon.

10. The system of claim 1, wherein the catheter includes at least three lumens including a third lumen for drainage, and at least one drainage port in the catheter that is in fluid communication with the third lumen and provides fluid communication between the third lumen and an exterior of the catheter.

11. The system of claim 1, wherein the suction member is in the form of a suction cup having a distally facing concave shape.

12. The system of claim 11, wherein the suction cup is flexible and resilient and biased to the distally facing concave shape, the suction cup being capable of temporarily folding over to have a concave shape facing proximally in response to insertion through a constriction, wherein the suction cup will return to the distally facing concave shape after passing through the constriction.

13. A method of treating postpartum hemorrhage, the method comprising;

delivering a medical device system to the interior of a body cavity, the system comprising:

an elongated catheter having a proximal and a distal end and an inflatable balloon attached to a distal portion of the catheter;

a suction member attached to the distal end of the catheter and disposed distally from the balloon;

delivering the catheter and suction member into the body cavity;

delivering the suction member into contact with an internal wall of the body cavity;

applying a suction force to the suction member via a suction lumen extending through the catheter;

in response to applying the suction force, anchoring the catheter to the internal wall of the body cavity;

in response to anchoring the catheter, inflating the balloon via an inflation port of the catheter.

14. The method of claim 13, wherein the catheter includes at least one proximal drainage port disposed proximally relative to the balloon and at least one distal drainage port disposed between the suction member and the balloon, the catheter includes a drainage lumen in fluid communication with the drainage ports, and wherein the method further comprises receiving fluid into the drainage lumen through each of the drainage ports.

15. The method of claim 14, wherein the system further comprises a stylet extending into the drainage lumen of the catheter, wherein the catheter and stylet are delivered together.

16. The method of claim 15, wherein the stylet includes a stylet lumen and proximal and distal passageways in fluid communication with the stylet lumen, the passageways aligned with the proximal and distal drainage ports when the stylet is inserted within the drainage lumen of the catheter, the method further comprising delivering a compound through the stylet lumen, through the passageways, and through the drainage ports into the body cavity.

17. The method of claim 15, wherein, after inflating the balloon, removing the stylet from the drainage lumen, and after removing the stylet, inserting the stylet into the drainage lumen and delivering a compound through a lumen of the stylet, through at least one passageway defined by the stylet, and through at least one of the proximal and distal drainage ports into the body cavity.

18. The method of claim 15, wherein the stylet is stiffer than the catheter.

19. The method of claim 15, wherein fluid from the body cavity drains through a lumen of the stylet via at least one passageway defined through a wall of the stylet.

* * * * *